United States Patent [19]
Ruminski

[11] Patent Number: 5,681,820
[45] Date of Patent: Oct. 28, 1997

[54] GUANIDINOALKYL GLYCINE β-AMINO ACIDS USEFUL FOR INHIBITING TUMOR METASTASIS

[75] Inventor: Peter Gerrard Ruminski, Ballwin, Mo.

[73] Assignee: G. D. Searle & Co., Chicago, Ill.

[21] Appl. No.: 442,268

[22] Filed: May 16, 1995

[51] Int. Cl.[6] .................. A61K 37/00; C07K 241/00
[52] U.S. Cl. .................. 514/18; 514/20; 514/616; 514/340; 514/357
[58] Field of Search .................. 514/20, 616, 18, 514/340, 357

[56] References Cited

U.S. PATENT DOCUMENTS

| | | | |
|---|---|---|---|
| 4,879,313 | 11/1989 | Tjeong et al. | 514/564 |
| 4,952,562 | 8/1990 | Klein et al. | 514/530 |

FOREIGN PATENT DOCUMENTS

| | | |
|---|---|---|
| 0 319 506 | 6/1989 | European Pat. Off. |
| WO 91/04746 | 4/1991 | WIPO |
| WO 92/13552 | 8/1992 | WIPO |
| WO 92/17196 | 10/1992 | WIPO |
| WO 93/09795 | 5/1993 | WIPO |

OTHER PUBLICATIONS

Fok et al. "Aminopeptidase resistant Arg–Gly–Asp analogs are stable in plasma inhibit platelet aggregation." *Int. J. Peptide Res.*, 38, 124–130 (1991).

Greenspoon et al. "Structural Analysis of Integrin–Mediated Cell Functions by Novel Nonpeptide Surrogates of the Arg–Gly–Asp Sequence." *Biochemistry*, 32, 1001–1008 (1993).

McDowell et al. "From Peptide to Non–Peptide. The Elucidation of a Bioactive Conformation of the Arg–Gly–Asp Acid Recognition Sequence." *J. Am. Chem. Soc.*, 116, 5069–5076 (1994).

*Primary Examiner*—Frederick Krass
*Attorney, Agent, or Firm*—Cynthia S. Kovacevic; Roger A. Williams

[57] ABSTRACT

This invention herein relates to a method of treating a condition mediated by inhibition of $\alpha_v\beta_3$ integrins and a method of inhibiting tumor metastasis by administering a therapeutically effective amount of a compound having the following formula

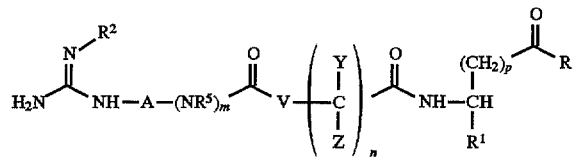

or a pharmaceutically acceptable salt thereof.

2 Claims, No Drawings

GUANIDINOALKYL GLYCINE β-AMINO ACIDS USEFUL FOR INHIBITING TUMOR METASTASIS

FIELD OF THE INVENTION

The present invention relates to a method for inhibiting tumor metastasis.

BACKGROUND OF THE INVENTION

Tumor cell invasion occurs by a three step process: 1) tumor cell attachment to the extracellular matrix; 2) proteolytic dissolution of the matrix; and 3) movement of the cells through the dissolved barrier. This process can occur repeatedly and can result in metastases at sites distant from the original tumor.

Integrins are a group of proteins which mediate cell adhesion and therefore are useful mediators of cell adhesion interactions which occur during the metastatic process. Integrins are composed of noncovalently linked α and β polypeptide subunits. Currently eleven different α subunits have been identified and six different β subunits have been identified. These various subunits can combine in various manners to form distinct integrins.

The $α_vβ_3$ integrin (also known as the vitronectin receptor) has been identified as an integrin which plays a role in the metastatic process. More specifically antagonism of the $α_vβ_3$ integrin has been associated with inhibition of tumor metastasis.

It has been shown that the $α_vβ_3$ integrin binds to a number of Arg-Gly-Asp- containing proteins (also known as RGD proteins). Compounds containing such sequence mimic extracellular matrix ligands so as to bind to cell surface receptors. However, RGD peptides in general are nonselective for RGD-dependent integrins. For example, most RGD peptides which bind to $α_vβ_3$ also bind to $α_vβ_5$ and $α_vβ_1$. Seftor et al. (Proc. Natl. Acad. Sci. USA 89 (1992) 1557–1561) have shown with melanoma cell assay research that the $α_vβ_3$ integrin has a biological function in melanoma cell invasion. Montgomery et al., (Proc. Natl. Acad. Sci USA 91 (1994) 8856–60) have demonstrated that the integrin $α_vβ_3$ expressed on human melanoma cells promotes a survival signal protecting the cells from apoptosis in a three-dimensional collagenous environment. Brooks et al. (Cell, V.79, 1157–1164) have demonstrated that antagonists of integrin $α_vβ_3$ may provide a therapeutic approach for the treatment of neoplasia since systemic administration of $α_vβ_3$ antagonists causes dramatic regression of various histologically distinct human tumors. Mediation of the tumor cell metastatic pathway by interference with the $α_vβ_3$ integrin cell adhesion receptor to impede tumor metastasis would be beneficial. It would be beneficial therefore to design compounds which are selective inhibitors or antagonists of the $α_vβ_3$ integrin.

European Patent Application 496,378 discloses amidino-biphenyl compounds which inhibit cell-cell and cell-matrix interaction and are useful for treating thrombosis, cerebrovascular diseases, pulmonary embolisms, myocardial infarction, arteriosclerosis, osteoporosis and tumour metastases.

WO 93/09795 discloses non-peptide RGD analogs having terminal guanidino and carboxyl functions spaced by a chain of 11 atoms, at least 5 of which are carbon atoms, and containing no sequence of α-amino acids. These compounds inhibit platelet aggregation and are useful for the treatment of several pathological disorders.

SUMMARY OF THE INVENTION

The present invention relates to a method of treating conditions mediated by inhibition or antagonism of $α_vβ_3$ integrins by administering to a mammal in need of such treatment a therapeutically effective amount of a compound selected from compounds represented by the formula:

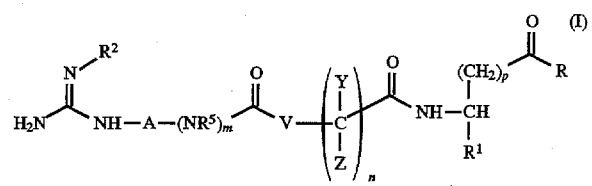

or a pharmaceutically acceptable salt thereof, wherein $R^2$ is selected from the group consisting of hydrogen, hydroxy, amino, alkoxy, lower alkyl and cyano;

A is selected from the group consisting of lower alkylene, lower alkenylene, and lower alkynylene which groups are optionally substituted by lower alkyl, lower alkenyl, lower alkynyl, cycloalkyl or aryl;

m is an integer 0 or 1;

$R^5$ is selected from the group consisting of hydrogen and lower alkyl;

V is selected from the group consisting of —$CH_2$—, —N($R_6$)—, and monocyclic N-containing heterocycles wherein $R^6$ is selected from the group consisting of H and lower alkyl;

Y and Z are independently selected from the group consisting of hydrogen, branched or straight lower alkyl and cycloalkyl;

n is an integer 0, 1, 2 or 3;

p is an integer 1, 2 or 3;

R is X—$R^3$ wherein X is selected from the group consisting of O, S and —$NR^4$, wherein $R^3$ and $R^4$ are independently selected from the group consisting of hydrogen, lower alkyl, aryl and arylalkyl; and $R^1$ is selected from the group consisting of alkyl, alkenyl, alkynyl, aryl, and monocyclic or bicyclic heterocycles wherein one to three carbon atoms are replaced by O, N or S.

Such a method is useful in treatment of conditions mediated by cell adhesion, for example, the inhibition of tumor metastasis.

DETAILED DESCRIPTION OF THE INVENTION

The present invention relates to a method for treating a condition mediated by antagonism or inhibition of $α_vβ_3$ integrins by administering to a mammal in need of such treatment a therapeutically effective amount of a compound selected from compounds represented by the formula I, described above.

A preferred embodiment of the present invention is a method of inhibiting tumor metastasis by administering to a mammal in need of such treatment a therapeutically effective amount of a compound of the formula I or a pharmaceutically acceptable salt thereof. A most preferred embodiment of the present invention is a method of inhibiting tumor metastasis by administering to a mammal in need of such treatment a therapeutically effective amount of a compound of the Formula I or a pharmaceutically acceptable salt thereof wherein A is lower alkyl and m is 0. Most preferably, the compound administered is a compound wherein A is lower alkyl; m is 0; R is —OH or alkoxy and $R^1$ is pyridyl.

Embodiments of compounds useful in the method of the present invention are the following compounds and pharmaceutically acceptable salts thereof:

methyl β-[[2-[[5-[(aminoiminomethyl)amino]-1-oxopentyl]amino]-1-oxoethyl]amino]-3-pyridinepropanoate;

β-[[2-[[5-[(aminoiminomethyl)amino]-1-oxopentyl]amino]-1-oxoethyl]amino]-3-pyridinepropanoic acid;

(±) ethyl β-[[2-[[4-[(aminoiminomethyl)amino]-1-oxobutyl]amino]-1-oxoethyl]amino]-3-pyridinepropanoate;

(±) β-[[2-[[4-[(aminoiminomethyl)amino]-1-oxobutyl]amino]-1-oxoethyl]amino]-3-pyridinepropanoic acid;

(±)ethyl β-[[2-[[6-[(aminoiminomethyl)amino]-1-oxohexyl]amino]-1-oxoethyl]amino]-3-pyridinepropanoate;

(±) β-[[2-[[6-[(aminoiminomethyl)amino]-1-oxohexyl]amino]-1-oxoethyl]amino]-3-pyridinepropanoic acid;

(±) β-[[3-[[4-[(aminoiminomethyl)amino]-1-oxobutyl]amino]-1-oxopropyl]amino]-3-pyridinepropanoic acid;

(±)ethyl β-[[2-[[4-[(aminoiminomethyl)amino]-1-oxo-3-phenylbutyl]amino]-1-oxoethyl]-amino]-3-pyridinepropanoate;

(±) β-[[2-[[4-[(aminoiminomethyl)amino]-1-oxo-3-phenylbutyl]amino]-1-oxoethyl]-amino]-3-pyridinepropanoic acid;

ethyl βS-[[[1-[5-[(aminoiminomethyl)amino]-1-oxopentyl]pyrrolidin-2-yl]carbonyl]-amino-3-pyridinepropanoate; and βS-[[[1-[5-[(aminoiminomethyl)amino]-1-oxopentyl]pyrrolidin-2-yl]carbonyl]-amino]-3-pyridinepropanoic acid.

As used herein, the terms "alkyl" or "lower alkyl" refer to a straight chain or branched chain hydrocarbon radicals having from about 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The terms "cycloalkyl" or "alicyclic hydrocarbon radical" as used herein mean a saturated or unsaturated cyclic carbon radical containing 3 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The terms "aryl," "arene," and "aromatic hydrocarbon radical" as used herein denote aromatic ring systems composed of one or more aromatic rings. Preferred aryl groups are those consisting of one, two or three aromatic rings. The term "aryl" embraces aromatic radicals such as phenyl, pyridyl, naphthyl, biphenyl and the like.

As used herein, the term "cyano" is represented by a radical of the formula ≹—CN.

The terms "hydroxy" and "hydroxyl" as used herein are synonomous and are represented by a radical of the formula ≹—OH.

As used herein the phrase "monocyclic or bicyclic heterocycle radicals" embraces monocyclic, or bicyclic radicals containing from 4 to about 12 atoms, and more preferably 5 to about 10 atoms, wherein 1 to 3 of the atoms are heteroatoms selected from the group consisting of oxygen, nitrogen and sulfur. Representative examples of heterocyclic radicals are furan, pyridine, benzofuran, pyran, thiophene, benzodioxole, benzothiophene and the like.

As used herein the term "monocyclic N-containing heterocycle" refers to monocyclic radicals containing from 3 to 7 atoms at least one of which is a nitrogen atom. Examples of such "monocyclic N-containing heterocycles" include piperidyl, piperizinyl, pyrrolidinyl and the like.

The symbol "BOC" as used herein refers to t-butoxycarbonyl.

The symbol "Δ" as used herein refers to heating the reaction mixture.

The abbreviation "DMF" as used herein means dimethylformamide.

The abbreviation "DIEA" as used herein refers to diisopropylethylamine.

The abbreviation "LiOH" as used herein refers to lithium hydroxide.

The abbreviation "TFA" as used herein refers to trifluoroacetic acid.

The term "lower alkylene" or "alkylene" as used herein refers to divalent linear or branched saturated hydrocarbon radicals of 1 to about 6 carbon atoms. The term "lower alkenylene" or "alkenylene" as used herein refers to divalent linear or branched hydrocarbon radicals containing at least one double bond and 2 to about 6 carbon atoms. As used herein the term "lower alkynylene" or "alkynylene" refers to divalent hydrocarbon radicals, linear or branched, containing one or more triple bonds and 2 to about 6 carbon atoms.

As used herein the term "alkoxy" refers to straight or branched chain oxy containing radicals of the formula —OR$_{10}$, wherein R$_{10}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the term "arylalkyl" refers to a radical of the formula R$_{11}$–R$_{12}$—≹ wherein R$_{11}$ is aryl as defined above and R$_{12}$ is an alkylene as defined above.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The compounds as shown in formula I can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of the pharmacologically acceptable salts may be prepared by conventional means. (See Berge et al., *J Pharm. Sci.*, 66(1), 1–19 (1977) for additional examples of pharmaceutically acceptable salts.)

For the inhibition or antagonism of $\alpha_v\beta_3$ integrins and more specifically for inhibition of tumor metastasis, compounds useful in the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds useful in the present invention are administered by any suitable route in the form of a pharmaceutical composition adapted to such a route, and in a dose effective for the treatment intended. Therapeutically effective doses of the compounds required to prevent or arrest the progress of the medical condition are readily ascertained by one of ordinary skill in the art.

Accordingly, the present invention provides a method of treating conditions mediated by inhibiting or antagonizing the $\alpha_v\beta_3$ cell surface receptor which method comprises administering a therapeutically effective amount of a compound selected from the class of compounds depicted in formula I wherein one or more compounds of the formula I is administered in association with one or more non-toxic, pharmaceutically acceptable carriers and/or diluents and/or adjuvants (collectively referred to herein as "carrier" materials) and if desired other active ingredients. More specifically, the present invention provides a method for inhibiting tumor metastasis by inhibition of the $\alpha_v\beta_3$ cell surface receptor.

The dosage regimen for inhibiting tumor metastasis with the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions.

The active ingredient administered by injection is formulated as a composition wherein, for example, saline, dextrose or water may be used as a suitable carrier. A suitable daily dose would typically be about 0.01 to 10 mg/kg body weight injected per day in multiple doses depending on the factors listed above.

For administration, the compounds are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The compounds of formula I may be prepared by standard synthetic methods combined with methods analogous to solution phase peptide synthesis [see: *The peptides: Analysis, Synthesis, Biology* (E. Gross and J. Meienhofer, eds.), Vol. 1–5, Academic Press, New York)].

The general synthetic sequences for preparing the compounds useful in the present invention are outlined in Schemes I–VI.

SCHEME I

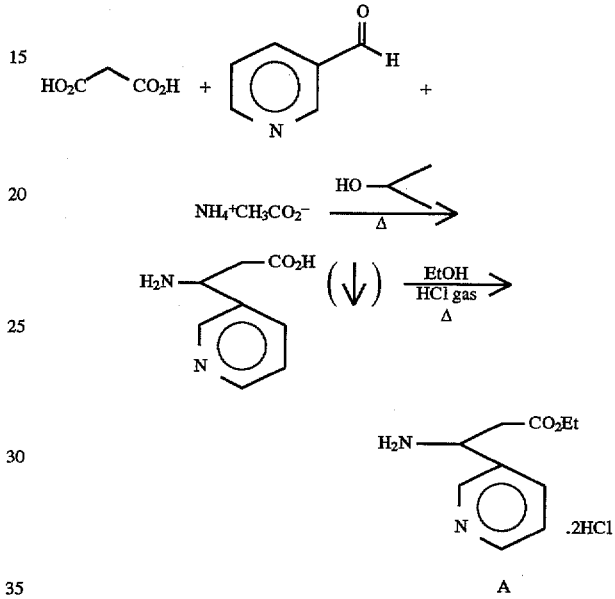

A

Scheme I describes a synthesis of a pyridyl β-aminoacid which can be used to synthesize compounds of the present invention wherein $R_1$ is pyridyl. The scheme can be modified using conventional methodology to prepare other aromatic, alkyl or heterocyclic substituted β-amino acids by substitution of the pyridyl carboxaldehyde with any other appropriate aldehyde. Briefly, in Scheme I to pyridinecarboxaldehyde in propanol is added ammonium acetate followed by malonic acid. The reaction mixture is stirred at reflux, the resulting precipitate filtered and washed with hot isopropanol and dried to yield 3-amino-3-(3-pyridyl) propionic acid.

Additionally, β-Amino acids which are useful in the present invention are accessible through modified Knoevenagel reactions (Secor, H. V.; Edwards, W. B. *J. J. Org. Chem.* 1979, 44, 3136–40; Bellasoued, M.; Arous-Chtar, R.; Gaudemar, M. J.; *J. Organometal. Chem.* 1982, 231, 185–9), through Reformatski reaction with Schiff bases (Furukawa, M.; Okawara, T.; Noguchi, Y.; Terawaki, Y. *Chem. Pharm. Bull.* 1978, 26, 260), Michael addition into an acrylic derivative (Davies, S. G.; Ichihara, O. *Tetrahedron:Asymmetry* 1991, 2, 183–6; Furukawa, M.; Okawara, T.; Terawki, Y. *Chem. Pharm. Bull.*, 1977, 25, 1319–25). More recent methods include the use of organometallic reagents in Pd or Zn mediated couplings (Konopelski, J.; Chu, K. S.; Negrete, G. R. *J. Org. Chem.* 1991, 56, 1355; Mokhallalati, M. K.; Wu, M- J.; Prigden, L. N. *Tetrahedron Lett.* 1993, 34, 47–50) to complement more traditional reactions such as reductive amination of β-ketoesters.

The racemic beta-alkyl beta amino esters can also conveniently be prepared from the corresponding beta lactam by treatment with anhydrous HCl gas in ethanol. The beta lactams were prepared from the corresponding alkene and chlorosulfonyl isocyanate (Szabo, W. A. *Aldrichimica Acta*, 1977, 23). The latter method is useful for the preparation of α and β-substituted β-aminoacids. (Manhas, M. S.; Wagle, D. R.; Chong, J.; Bose, A. K. *Heterocycles*, 1988, 27, 1755.) Another route to α-substituted β-aminoacids is the Raney Nickel reduction of cyanoacetic esters at temperatures ranging between 20° and 80° C. and at 20 to 100 atm pressure (Testa, E.; Fontanella, L.; Fava, F. *Fermaco Ed. Sci.*, 1958, 13, 152; Testa, E.; Fontanella, L. *Annalen* 1959, 625, 95). Also, a number of procedures are available for the preparation of β-aminoacids by reduction of hydrazones of ketoacids (Gootijes, J.; Nomte, W. Th. *Rec. Tray. Chem.* 1953, 72, 721), oximes (Anziegin, A.; Gulewivich, W. Z. *Physiol. Chem.*, 1926, 158, 32) and nitropropionic acids. Purification of final compounds is usually by reverse phase high performance liquid chromatography (RP HPLC)[High Performance Liquid Chromatography Protein and Peptide Chemistry, F. Lottspeich, A. Henscher, K. P. Hupe, (eds.) Walter DeGruyter, New York, 1981] or crystallization.

SCHEME II

A + BOCNH⌒CO$_2$H +

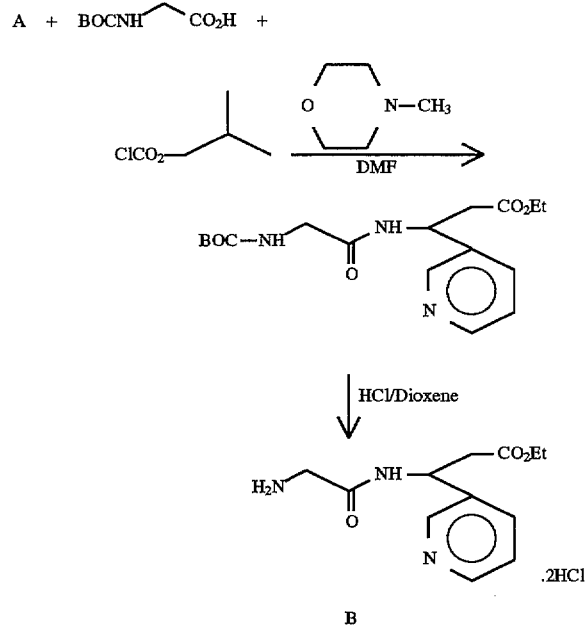

B

Scheme II is illustrative of methodology useful for coupling an α-amino acid to the β-amino acid compounds prepared in Scheme I. The compounds thus prepared are useful for coupling to guanidino-alkanoic and cycloalkanoic acid compounds to prepare the desired compounds of the present invention. Such methodology can be modified using conventional methodology to couple other aminoalkyl acids to the β-amino acids prepared in Scheme I.

Briefly, in Scheme II, to a solution of BOC-glycine in DMF is added 1-methyl morpholine followed by isobutylchloroformate. In a separate flask, the substituted β-amino acid in DMF is mixed with 1-methylmorpholine. The two mixtures are combined and stirred overnight to yield

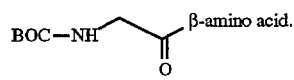

The resulting product is deprotected using HCl/Dioxane.

SCHEME III

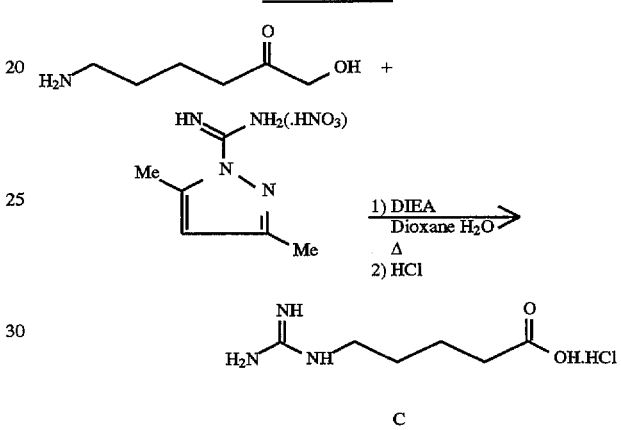

C

Scheme III is illustrative of methodology useful for preparing the guanidinoalkanoic acid or guanidinocycloalkanoic acid portion of the present invention which can be used for coupling to the β-amino acid. This can also be accomplished using other appropriate guanidating reagents known to those skilled in the art. The methodology of Scheme III can be modified using conventional techniques and methods to prepare alternate compounds useful for coupling to the β-amino acids.

Briefly, in Scheme III, to 3,5-dimethylpyrazole-1-carboxamidine nitrate in dioxane, water and DIEA, is added 5-aminovaleric acid. The mixture is stirred at reflux, the precipitate filtered, washed and dried. The precipitate is then further slurried in water, acidified and concentrated. The solvent is removed and the residue slurried and dried to yield 5-guanidinovaleric acid hydrochloride.

SCHEME IV

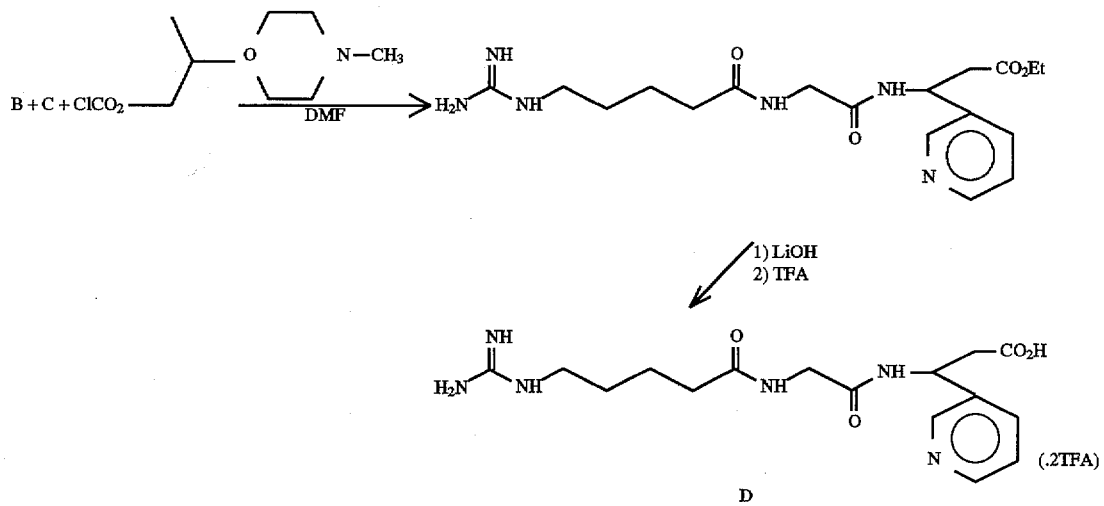

Scheme IV illustrates methodology useful for coupling the guanidino-alkyl acid to the β-amino acid portion of the desired compounds of the present invention. Such methodology can be modified using conventional methods known to those having ordinary skill in the art.

Briefly, in Scheme IV to the 5-guanidinovaleric acid (prepared in Scheme III) in DMF and N-methylmorpholine was added isobutylchloroformate. The reaction was stirred and a slurry of the β-amino acid compound (prepared in Scheme II) in DMF and N-methylmorpholine was added portionwise. The reaction was stirred, the precipitate filtered and washed with DMF. The DMF was removed. The resulting ester is dissolved in water, washed and LiOH is added to the aqueous layer and stirred. The solution is washed and treated with trifluoroacetic acid to pH=5. The solvent is removed and the product purified by RPHPLC to yield the desired compounds.

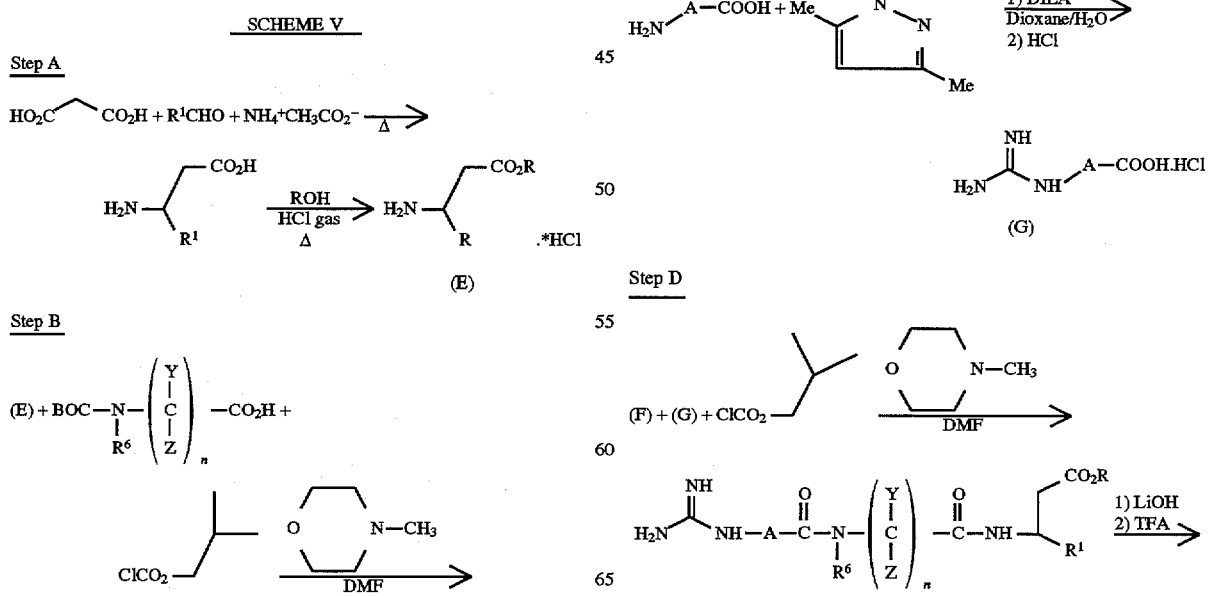

5,681,820

-continued
SCHEME V

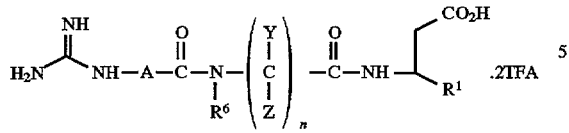

SCHEME VI

[for (NR$^5$)$_m$, where m = 1, V = CH$_2$]

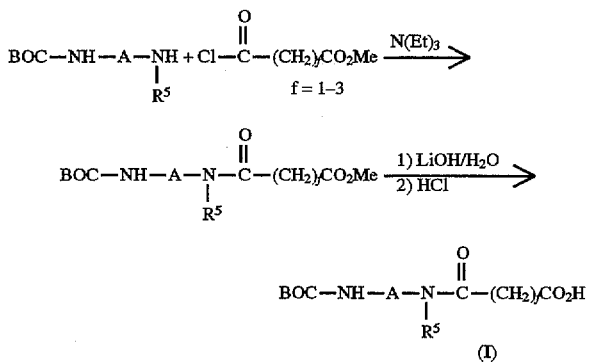

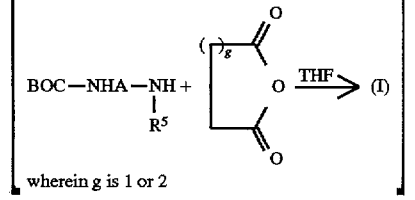

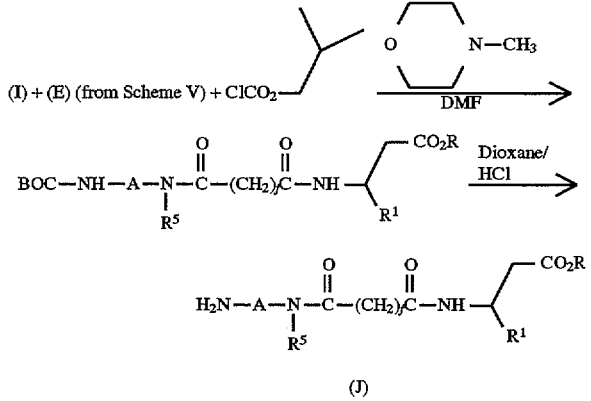

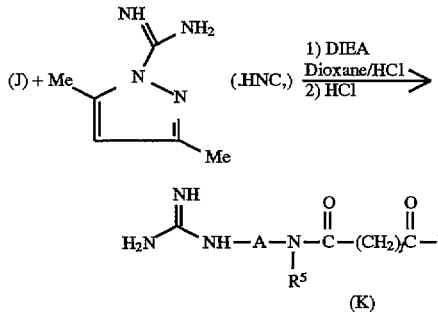

(K) + LiOH $\xrightarrow{\text{TFA}}$

-continued
SCHEME VI

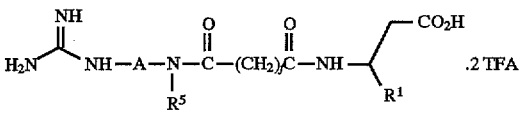

[For (NR$_5$)$_m$, where m = 1 and V = N—R$^6$ where R$^6$ = H can be made as in Scheme VI but substituting O=C=N—(CH$_2$)$_f$CO$_2$Me for
$$Cl-\overset{O}{\underset{\|}{C}}(CH_2)fCO_2Me \text{ in the first Step.}$$]

Schemes V and VI are illustrative of methodology useful for preparing various compounds of the present invention. Such methodology is more specifically defined in Schemes I–IV and the following Examples. Such methodology can be modified by one skilled in the art, substituting known reagents and conditions from conventional methodology to produce the desired compounds.

The following non-limiting examples describe and illustrate the methods for the preparation of the compounds useful in the present invention, as well as other aspects of the present invention, and the results achieved thereby, in further detail. Both an explanation of, and the actual procedures for, the various aspects of the present invention are described where appropriate. These examples are intended to be merely illustrative of compounds useful in the present invention, and not limiting thereof in either scope or spirit. Those of skill in the art will readily understand that known variations of the conditions and processes of the preparative procedures described in these examples can be used to prepare the compounds useful in the present invention, and the pharmaceutical compositions comprising such compounds.

All the starting materials used in the examples are commercially available (or can be prepared by known methodology) as is all the equipment employed in the examples.

EXAMPLE 1

β-[[2-[[5-[(aminoiminomethyl)amino]-1-oxopentyl]amino]-1-oxoethyl]amino]-3-pyridinepropanoic acid, bistrifluoroacetate salt

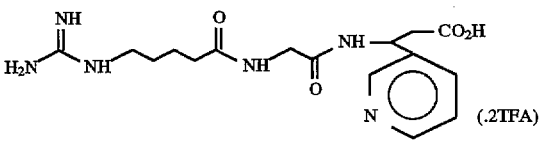

Step A

To 300 ml of 3-pyridine carboxaldehyde in 3 liters of 2-propanol was added 297 g of ammonium acetate followed by 398 g of malonic acid. The reaction mixture was stirred at reflux for 5 hours. The precipitate was filtered while hot and washed with 2 liters of hot isopropanol. The resulting white solid was then dried to yield 220 g of DL-3-amino-3-(3-pyridyl)propionic acid as a white solid.

NMR and MS were consistent with the desired product.

Step B 220 g of DL-3-amino-3-(3-pyridyl)propionic acid from Step A was slurried in 3.6 liters of absolute EtOH. One lecture bottle (½ lb) of HCl gas was bubbled into the reaction while stirring over 40 minutes (slow exotherm to 61° C.). The slurry was then heated at reflux for 4 hours (a solution forms after 1 to 1.5 hours). The reaction mixture was cooled to 5° C. in an ice bath. After stirring at 5° C. for 1.5 hours, the resulting white precipitate was filtered and washed thoroughly with ether. After drying under vacuum at 50° C., the yield of DL-ethyl-3-amino-3-(3-pyridyl)propionate dihydrochloride was 331.3 g as a white solid.

NMR and MS are consistent with the desired product.

Step C

To 220.6 g (0.83 mole) of DL-ethyl-3-amino-3-(3-pyridyl)-propionate dihydrochloride from Step B in 2 liters of anhydrous THF and 167.2 g (1.65 moles) of triethylamine, 225 g (0.826 moles) of N-t-BOC-glycine N-hydroxysuccinimide ester (Sigma) was added in several portions at 5°–10° C. (no exotherm). The reaction mixture was stirred overnight at room temperature. The resulting precipitate was filtered and washed with THF. The solvent from the filtrate was then removed under vacuum. The residue was taken up in 2.3 liters of ethyl acetate. The ethyl acetate layer was washed with saturated sodium bicarbonate (2×900 ml) and $H_2O$ (3×900 ml), dried over $MgSO_4$ and removed under vacuum. The residue was slurried overnight in 2.5 liters of 10% ethyl acetate/hexane. The precipitate was filtered, washed with 1 liter of 10% ethyl acetate/hexane, then hexane, then dried to yield 233 g of ethyl β-[[2-[[(1,1-dimethylethoxy) carbonyl]amino]-1-oxoethyl]amino] pyridine-3-propanoate as a white solid.

NMR and MS are consistent with the desired structure.

Step D 232 g (0.66 mole) of ethyl β-[[2-[[(1,1-dimethylethoxy) carbonyl]amino]-1-oxoethyl]amino]-pyridine-3-propanoate (from Step C) was dissolved in 1 liter of warm dioxane. After cooling to room temperature, 1.6 liters of 4M HCl in dioxane (Aldrich) was slowly added. A white precipitate formed after several minutes and then turned to a thick goo. After 2 hours, the solvent was decanted off. Ether was slurried and decanted several times until a white solid resulted. This was dried under vacuum to yield 224.2 g of ethyl β-[(2-amino-1-oxoethyl)amino]pyridine-3-propanoate, bis(hydrochloride) salt as a white hygroscopic solid.

NMR and MS are consistent with the desired structure.

Step E

To 325 g (1.63 mole) of 3,5-dimethylpyrazole-1-carboxamidine nitrate (Aldrich) in 975 ml dioxane, 390 ml $H_2O$ and 283 ml (1.63 mole) diisopropylethylamine was added 121.6 g (1.04 mole) of 5-aminovaleric acid. This mixture was stirred at reflux for 1 hour and then at room temperature overnight. The precipitate was filtered, washed with 500 ml of dioxane and then washed with 1 liter of dioxane:$H_2O$ (1:1). The precipitate was air dried, then slurried in 500 ml $H_2O$ and acidified to pH=1 with concentrated HCl which resulted in a solution. The solvent was removed under vacuum and the residue slurried several times with ether (ether decanted off) and dried under vacuum to yield 179.8 g of 5-guanidino valeric acid hydrochloride as a white solid.

NMR and MS are consistent with the desired structure.

Step F

To 123.5 g (0.631 mole) of 5-guanidino valeric acid hydrochloride (from Step E) in 800 ml of anhydrous DMF (Aldrich) and 63.8 g (0.631 mole) of N-methyl morpholine was added dropwise over 10 minutes 88 g (0.631 mole) of isobutylchloroformate at 0°–5° C. (temperature kept below 15° C. during the addition with ice bath cooling). After stirring at ice bath temperature 5 additional minutes, a slurry was made up of 204.5 g (0.631 mole) ethyl β-[(2-amino-1-oxoethyl)amino]pyridine-3-propanoate, bis (hydrochloride) salt (from Step D) in 800 ml anhydrous DMF and 127.7 g (1.26 mole) N-methyl morpholine was added in several portions, keeping the reaction temperature below 20° C. with ice bath cooling. After addition was complete, the reaction was stirred overnight at room temperature. The precipitate was filtered off and washed with DMF. The DMF from the filtrate was removed under vacuum on a 75° C. water bath.

The residual ester was dissolved in 500 ml of warm $H_2O$. The $H_2O$ layer was washed 3 times with ethyl acetate and the ethyl acetate was discarded. To the aqueous layer was added 100 g of LiOH and this mixture was stirred at room temperature for 1.5 hours. The aqueous solution was washed 2 times with ether (ether discarded) and the aqueous layer was adjusted to pH=5 with trifluoroacetic acid. The solvent was removed under vacuum and the crude product was purified by reverse phase (C-18) preparative HPLC to yield 170 g of β-[[2-[[5-[(aminoiminomethyl)amino]-1-oxopentyl]amino]-1-oxoethyl]amino]-3-pyridinepropanoic acid, bistrifluoroacetate salt as a white solid.

NMR and MS are consistent with the desired structure.

EXAMPLE 2

βS-[[[1-[5-[(aminoiminomethyl)amino]-1-oxopentyl]pyrrolidin-2-yl]carbonyl]amino-3-pyridinepropanoic acid, bistrifluoroacetate salt

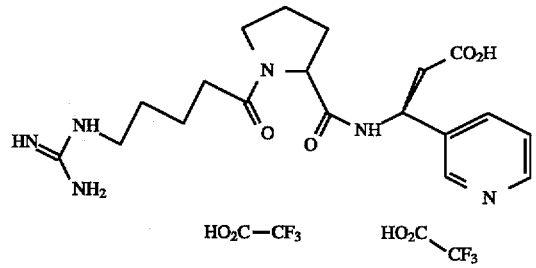

The above compound was prepared according to the method of Example 1 substituting 257.9 g of N-t-BOC-L-proline N-hydroxysuccinimide ester for N-t-BOC-glycine. N-hydroxysuccinimide ester in Step C.

NMR and MS were consistent with the desired structure.

EXAMPLE 3

(±) β-[[2-[[4-[(aminoiminomethyl)amino]-1-oxobutyl]amino]-1-oxoethyl]amino]-3-pyridinepropanoic acid, bistrifluoroacetate salt

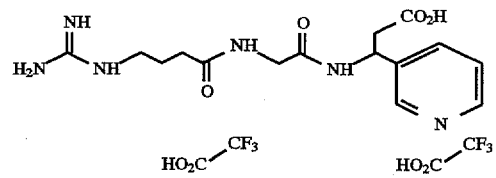

The above compound was prepared according to the methodology of Example 1 substituting 107.2 g of 4-aminobutanoic acid for the 5-aminovaleric acid in Step E.

NMR and MS are consistent with the desired structure.

EXAMPLE 4

(±) β-[[2-[[6-[(aminoiminomethyl)amino]-1-oxohexyl]amino]-1-oxoethyl]amino]-3-pyridinepropanoic acid, bistrifluoroacetate salt

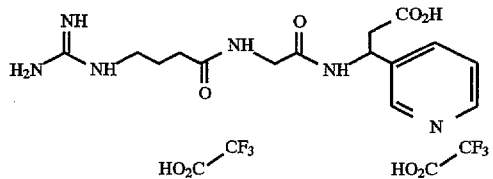

The above compound was prepared according to the methodology of Example 1 substituting 136.4 g of 6-aminohexanoic acid for the 5-aminovaleric acid in Step E.

NMR and MS are consistent with the desired structure.

EXAMPLE 5

(±) β-[[3-[[4-[(aminoiminomethyl)amino]-1-oxobutyl]amino]-1-oxopropyl]amino]-3-pyridinepropanoic acid, bistrifluoroacetate salt

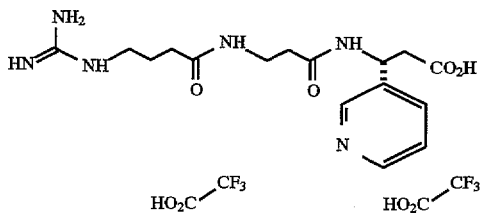

The above compound was prepared according to the method of Example 3 substituting 236.5 g of N-t-BOC-β-alanine-N-hydroxysuccinimide ester for N-t-BOC-glycine N-hydroxysuccinimide ester in Step C.

NMR and MS are consistent with the desired structure.

EXAMPLE 6

(±) β-[[2-[[4-[(aminoiminomethyl)amino]-1-oxo-3-phenylbutyl]amino]-1-oxoethyl]amino]-3-pyridinepropanoic acid, bistrifluoroacetate salt

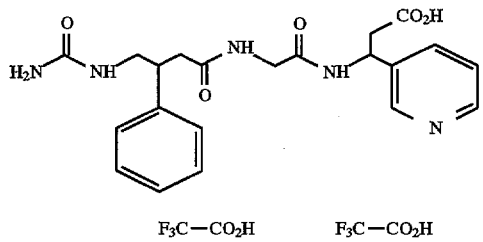

Step A 4-guinidino-3-p-chlorophenylbutyric acid hydrochloride was made using the method of Example 1 Step E, substituting 222.2 g of 4-amino-3-p-chlorophenylbutyric acid (RBI) for 5-aminovaleric acid. This product was reduced with 10% Pd/C in 50% EtOH/$H_2O$ under 50 psi $H_2$ overnight to yield 4-guanidino-3-phenylbutyric acid hydrochloride.

Step B

The title compound of Example 6 was made as in Example 1 Step F, substituting 162.6 g of the product of Example 6 Step A above for 5-guanidinovaleric acid hydrochloride.

NMR and MS are consistent with the desired structure.

The activity of the compounds used in the present invention is demonstrated by the following cell adhesion assays. The results of such cell adhesion assays are tabulated in Table 1.

M21 Melanoma Cell Adhesion Assasy

This assay involves an $\alpha_v\beta_3$-dependent adhesion of M21 human melanoma cells to human fibrinogen-coated plastic tissue culture dishes.

Fibrinogen was purified from human plasma. Fibronectin and plasminogen were eliminated from the preparation by passing the sample over gelatin-sepharose 4B and lysine-sepharose 4B resins, respectively. The fibrinogen is diluted to 10 μg/mL in coating buffer (20 mM Tris-HCl, 150 mM NaCl, pH 7.4). 100 μL of diluted fibrinogen is added to each well of a 96-well Immulon 2 microtiter plate (Dynatech; Chantilly, Va.) and allowed to coat overnight at 4° C. Plates are blocked with 1% BSA (Miles/Pentex; Kankakee, Ill.) in adhesion buffer (Hank's balanced salt solution without $Ca^{++}$ or $Mg^{++}$ [HBSS———], 50 mM Hepes, 1 mg/mL BSA, pH 7.4) for 1 hour at 37° C.

M21 human melanoma cells were provided by Dr. J. Smith, La Jolla Cancer Research Institute. M21 cells are harvested from tissue culture flasks by washing with HBSS——— and adding cell dissociation solution (Sigma) and incubating for 5 minutes at 37° C. Harvested cells are washed 3 times with adhesion assay buffer containing 200 μM $Mn^{++}$. Cells are counted and suspended to a density of $2 \times 10^6$/mL in adhesion assay buffer containing 200 μM $Mn^{++}$. M21 cells are pre-incubated with inhibitors of $\alpha_v\beta_3$ for 30 minutes at room temperature. Following the pre-incubation, the solutions containing a mixture of cells and inhibitors are added to each well of the microtiter plate and allowed to bind for 30 minutes at 37° C.

Following adhesion, plates are gently washed 3 times with 200 μL of wash buffer (50 mM Tris-HCl, 150 mM NaCl, pH 7.4) using large bore pipet tips. Plates are briefly blotted dry and 100 μL of cell lysis buffer (50 mM sodium acetate, pH 5.0, 0.5% Triton X-100, 0.3 mg/mL p-nitrophenyl phosphate [Sigma] is added to each well. Plates are incubated for 60 minutes at 37° C. and 50 μL of 1N NaOH is added to stop the reaction. The absorbance of the wells at 412 nM is read using an automatic plate reader.

Cell Adhesion Assays

Fibrinogen was purified from human plasma. Fibronectin and plasminogen were eliminated from the preparation by passing the sample over gelatin-sepharose 4B and lysine-sepharose 4B resins, respectively. The fibrinogen was resuspended at a concentration of 10 μg/mL in 100 mM sodium bicarbonate, pH 9.0. Immulon II (Nunc) microtiter plates were coated by incubating with 100 μL/well of fibrinogen solution overnight at 4° C. After coating with fibrinogen, plates were rinsed three times with phosphate buffered saline (PBS) and 100 μL of a 1% bovine serum albumin (BSA) solution was added to each well and stored at –20° C. until needed. A3827 cells were harvested from subconfluent 75 $cm^2$ culture flasks with 2 mM EDTA in PBS and resuspended at $5 \times 10^5$ cells/mL in Dulbecco's PBS without calcium or magnesium (Sigma #5652) containing 1% BSA. $MnCl_2$ was added to a final concentration of 300 μM. Test compounds were resuspended in PBS and added to the cell suspension before serial dilution. A 100 μL aliquot was added to each well and incubated at 37° C. for 1 hour. Nonadherant cells were removed by aspiration and wells were rinsed three times with PBS. Adherent cells were quantitated using a non-radioactive cell proliferation assay (Promega #G5430) using the instructions provided by the supplier. Plates were allowed to equilibrate overnight at room temperature in a humidified chamber and a Biotek EL312 microplate spectrophotometer was used to measure the difference in absorbance at 560 and 605 nM.

Cell Culture

A3827 cells were maintained in Dulbecco's Modified Eagles Medium (DME; Gibco-BRL #3201965PK) supplemented with 10% fetal bovine serum (FBS; Hyclone #A-1115-L) at 37° C. in 6% $CO_2$. Cells were fed fresh medium every 2–3 days and were passaged weekly by splitting at 1:10 dilutions after removal from substrate with trypsin/EDTA. Cells were split in the same manner at 1:5 dilutions one day prior to use in an assay.

Materials

Human vitronectin receptor($\alpha_v\beta_3$) was purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). GRGDSP peptide was purchased from Bachem (Torrance, Calif.). Linbro microtiter plates were obtained from Flow Labs (McLean, Va.). ADP reagent was obtained from Sigma (St. Louis, Mo.).

METHODS

Solid Phase Receptor Assays

This assay was essentially the same as previously reported [Niiya et al., *Blood*, 70:475–483 (1987)]. The purified human vitronectin receptor ($\alpha_v\beta_3$) was diluted from stock solutions to 1.0 µg/mL in Tris-buffered saline containing 1.0 mM $Ca^{++}$, $Mg^{++}$, and $Mn^{++}$, pH 7.4 (TBS+++). The diluted receptor was immediately transferred to Linbro microtiter plates at 100 µL/well (100 ng receptor/well). The plates were sealed and incubated overnight at 4° C. to allow the receptor to bind to the wells. All remaining steps were at room temperature. The assay plates were emptied and 200 µL of 1% RIA grade BSA in TBS+++ (TBS+++/BSA) were added to block exposed plastic surfaces. Following a 2 hour incubation, the assay plates were washed with TBS+++ using a 96 well plate washer. Logarithmic serial dilution of the test compound and controls were made starting at a stock concentration of 2 mM and using 2 nM biotinylated vitronectin in TBS+++/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was $1.0\times10^{-4}$M. The competition occurred for two hours after which all wells were washed with a plate washer as before. Affinity purified horseradish peroxidase labeled goat anti-biotin antibody was diluted 1:3000 in TBS+++/BSA and 125 µL were added to each well. After 30 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and %CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency*, Vienna, pp 469 (1977)], plotted on a semi-log scale, and the computed $IC_{50}$ and corresponding $R_2$ was reported. GRGDSP, a peptide fragment of fibrinogen, was included on each plate as a positive control.

The ester compounds disclosed as useful in the method of the present invention are prodrugs of the acid compounds which exhibit activity in these assays as indicated in Table I.

TABLE I

| Ex. # | VnR/IC50 (nM)* | A3827 IC50 (nM) | M21 IC50 (nM) |
| --- | --- | --- | --- |
| 1 | 9.4 | 30 | 40.4 |
| 2 | 142 | | |
| 3-ethyl ester | 987 | | 1410 |
| 3 | 23.1 | | |
| 4 | 460 | | |
| 5 | 706 | | |
| 6 | 31.6 | | |

*Purified $\alpha_v\beta_3$ Receptor Assay

What is claimed is:

1. A method of inhibiting tumor metastasis comprising administering to a mammal in need of such treatment a therapeutically effective amount of a compound of the formula

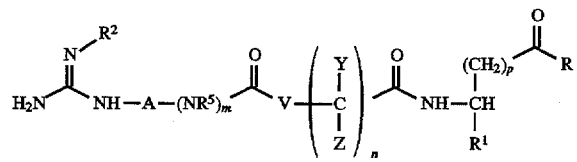

or a pharmaceutically acceptable salt thereof wherein $R^2$ is selected from the group consisting of hydrogen, hydroxy, amino, alkoxy, lower alkyl and cyano;

A is selected from the group consisting of lower alkylene, lower alkenylene, and lower alkynylene which groups are optionally substituted by lower alkyl, lower alkenyl, lower alkynyl, cycloalkyl or aryl;

m is an integer 0 or 1;

$R^5$ is selected from the group consisting of hydrogen and lower alkyl;

V is selected from the group consisting of —$CH_2$—, —N($R_6$)—, and monocyclic N-containing heterocycles, wherein $R^6$ is selected from the group consisting of H and lower alkyl;

Y and Z are independently selected from the group consisting of hydrogen, branched or straight lower alkyl and cycloalkyl;

n is an integer selected from 0, 1, 2 or 3;

p is an integer selected from 1, 2 or 3;

R is X—$R^3$ wherein X is selected from the group consisting of O, S and —$NR^4$, wherein $R^3$ and $R^4$ are independently selected from the group consisting of hydrogen, lower alkyl, aryl and arylalkyl; and R¹ is pyridyl.

2. A method of inhibiting tumor metastasis comprising administering to a mammal in need of such treatment a therapeutically effective amount of a compound selected from the group consisting of methyl β-[[2-[[5-[(aminoiminomethyl)amino]-1-oxopentyl]amino]-1-oxoethyl]amino]-3-pyridinepropanoate;

β-[[2-[[5-[(aminoiminomethyl)amino]-1-oxopentyl]amino]-1-oxoethyl]amino]-3-pyridinepropanoic acid;

(±) ethyl β-[[2-[[4-[(aminoiminomethyl)amino]-1-oxobutyl]amino]-1-oxoethyl]amino]-3-pyridinepropanoate;

(±) β-[[2-[[4-[(aminoiminomethyl)amino]-1-oxobutyl]amino]-1-oxoethyl]amino]-3-pyridinepropanoic acid;

(±)ethyl β-[[2-[[6-[(aminoiminomethyl)amino]-1-oxohexyl]amino]-1-oxoethyl]amino]-3-pyridinepropanoate;

(±) β-[[2-[[6-[(aminoiminomethyl)amino]-1-oxohexyl]amino]-1-oxoethyl]amino]-3-pyridinepropanoic acid;

(±) β-[[3-[[4-[(aminoiminomethyl)amino]-1-oxobutyl]amino]-1-oxopropyl]amino]-3-pyridinepropanoic acid;

(±)ethyl β-[[2-[[4-[(aminoiminomethyl)amino]-1-oxo-3-phenylbutyl]amino]-1-oxoethyl]-amino]-3-pyridinepropanoate;

(±) β-[[2-[[4-[(aminoiminomethyl)amino]-1-oxo-3-phenylbutyl]amino]-1-oxoethyl]-amino]-3-pyridinepropanoic acid;

ethyl βS-[[[1-[5-[(aminoiminomethyl)amino]-1-oxopentyl]pyrrolidin-2-yl]carbonyl]-amino]-3-pyridinepropanoate; and βS-[[[1-[5-[(aminoiminomethyl)amino]-1-oxopentyl]pyrrolidin-2-yl]carbonyl]-amino]-3-pyridinepropanoic acid.

* * * * *